(12) United States Patent
Ellison

(10) Patent No.: US 7,281,924 B2
(45) Date of Patent: Oct. 16, 2007

(54) APPARATUS AND METHOD FOR ANCHORING A DENTAL APPLIANCE

(75) Inventor: James T. Ellison, Johnston, RI (US)

(73) Assignee: Sterngold, Attleboro, MA (US)

( * ) Notice: Subject to any disclaimer, the term of this patent is extended or adjusted under 35 U.S.C. 154(b) by 271 days.

(21) Appl. No.: 11/118,601

(22) Filed: Feb. 23, 2004

(65) Prior Publication Data

US 2006/0160047 A1    Jul. 20, 2006

Related U.S. Application Data

(63) Continuation of application No. 09/970,201, filed on Oct. 4, 2001, now Pat. No. 6,695,616.

(51) Int. Cl.
*A61C 8/00* (2006.01)

(52) U.S. Cl. ..................... 433/174; 433/173

(58) Field of Classification Search ......... 433/172–176
See application file for complete search history.

(56) References Cited

U.S. PATENT DOCUMENTS

| 4,362,509 A | 12/1982 | Sulc |
| 4,540,367 A | 9/1985 | Sulc |
| 4,713,004 A | 12/1987 | Linkow et al. |
| 4,934,935 A | 6/1990 | Edwards |
| 5,100,323 A | 3/1992 | Friedman |
| 5,195,891 A | 3/1993 | Sulc |
| 5,199,873 A * | 4/1993 | Schulte et al. ............. 433/174 |
| 5,749,732 A | 5/1998 | Sendax |
| 6,375,465 B1 | 4/2002 | Engman et al. |
| 6,695,616 B2 | 2/2004 | Ellison |

FOREIGN PATENT DOCUMENTS

| DE | 94 19 173 U1 | 2/1995 |
| FR | 2 785 788 A | 5/2000 |

* cited by examiner

*Primary Examiner*—Cary E. O'Connor
(74) *Attorney, Agent, or Firm*—Patton Boggs LLP

(57) ABSTRACT

An anchor apparatus having a threaded post for threaded engagement with bone, and an upper circular receptacle. An angled support having a lower circular base and an upper female prosthesis receptacle is secured within to the implant anchor, the securing being through lower circular base being engaged with and adhered to the upper circular receptacle of the implant anchor. The circular base has a first longitudinal axis and the upper female prosthesis receptacle has a second longitudinal axis forming a mounting angle with respect to one another. A dental prosthesis having a male extension shaped for cooperative engagement with the upper female prosthesis receptacle of the implant anchor is secured to the implant anchor by such cooperative engagement. An alternate embodiment integrates the threaded post and the female prosthesis receptacle into a single member, for a zero degree angle.

5 Claims, 4 Drawing Sheets

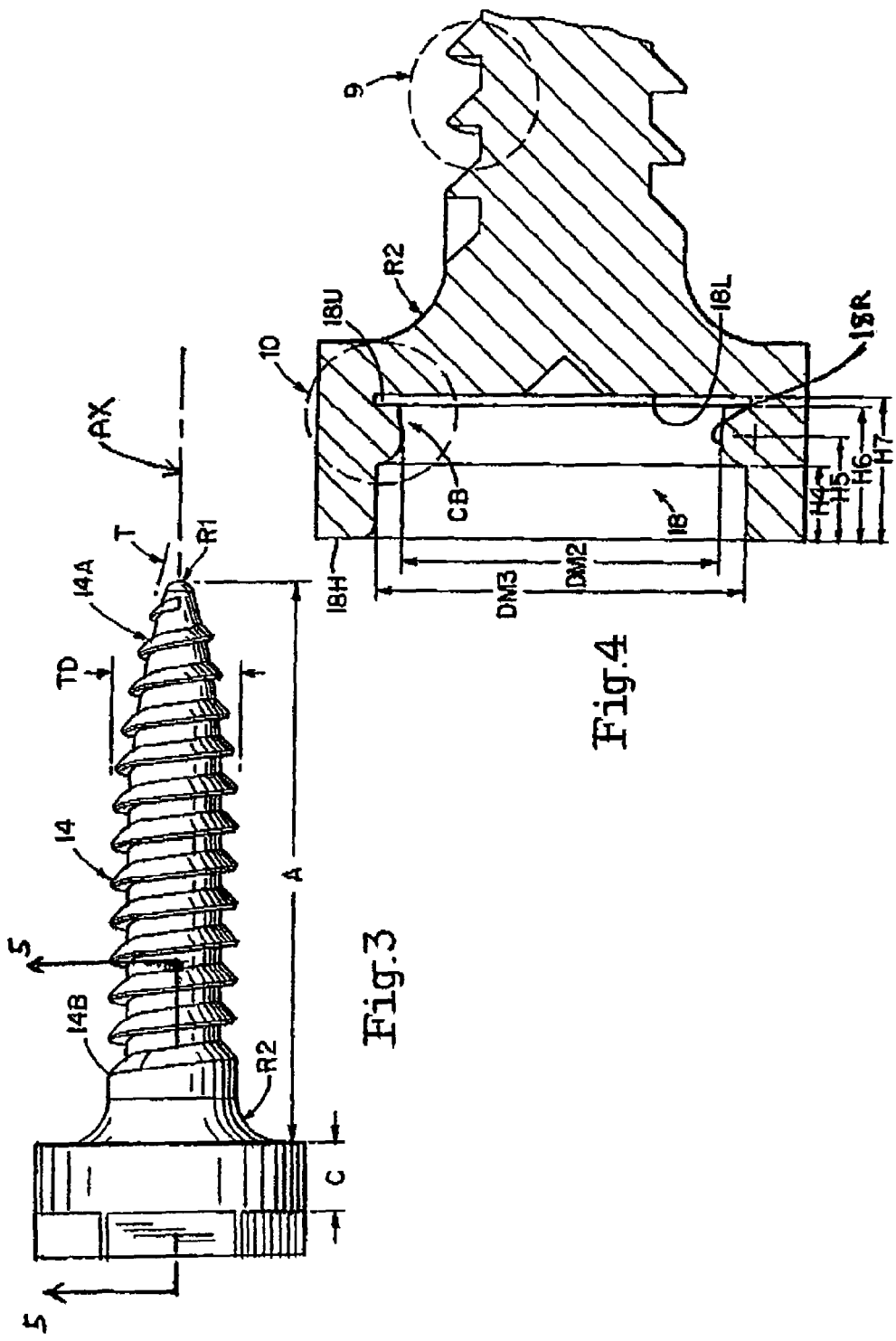

General reference no. "50" added

Reference no. "248" deleted.

Reference no. "18R" added

US 7,281,924 B2

APPARATUS AND METHOD FOR ANCHORING A DENTAL APPLIANCE

The following is a continuation of Ser. No. 09/970,201, filed on Oct. 4, 2001 now U.S. Pat. No. 6,695,616.

FIELD OF THE INVENTION

The present invention is directed toward a method and apparatus for an implant anchor for a dental prosthesis and, more particularly, a one-piece threaded implant anchor with an upper receptacle, for insertion into an oral cavity, into which an angled or straight prosthesis support is secured, for removable attachment of a dental prosthesis.

RELATED ART

Various methods and structures for anchoring appliances in the oral cavity are known in the art. For example, U.S. Pat. No. 4,540,367, issued to Sulc, ("the '367 Sulc patent") describes a multi-piece apparatus having a female member which attaches to a surface of a tooth adjacent to an apparatus anchoring site. Also shown in the '367 Sulc patent is an oral appliance containing a male member which attaches to the female member. The apparatus and method described by the '367 Sulc patent, although particularly useful for attaching to a dental surface adjacent to a desired anchoring site, is not optimal for all anchoring requirements.

Another anchoring method and apparatus is described by U.S. Pat. No. 5,749,732, issued to Sendax ("the Sendax patent" or "Sendax"). The apparatus described by the Sendax patent comprises a threaded anchor post having a square male upper extension. Using a wrench having a square socket, the threaded portion is rotated to attain threaded engagement with a bone. After the threaded portion has penetrated the bone to a suitable depth the square male upper extension remains above the gum. The threaded post portion has a lower threaded portion and an upper threaded portion separated by an unthreaded land. The Sendax patent describes the unthreaded land as functioning to assist bone growth engagement, thereby securing the anchor from unthreading. The square upper extension mates with, and is secured by adhesive to an oral appliance having a corresponding square receptacle.

There are commercially available anchors similar to the device described by Sendax but without the unthreaded land.

The apparatus and method described by the Sendax patent, and the similarly structured commercial products have shortcomings. One is that the upper extension and its cooperative fit with a dental appliance offers little, if any, adjustment after insertion. More particularly, the orientation of the upper extension is fixed by the rotational angle and insertion angle of the threaded portion. The orientation of the receptacle in the dental appliance, which is shaped to correspond to the upper extension, is also fixed relative to the appliance. However, after the threaded portion is screwed into the recipient's bone, changing its angle requires removal and re-insertion. After a period of time bone growth fixes the rotational position as well. Therefore, after insertion of the threaded anchor the angle and position of the dental appliance is substantially fixed.

Various methods and apparati for adjusting the angle of a dental appliance anchor are known. For example, U.S. Pat. No. 4,713,04, issued to Linkow et. al ("Linkow") discloses an implant placed in the bone and rotated into a proper orientation. Linkow shows a wedge shaped collar having an angled upper surface, which is described as positioned to coincide with the angle of the shaft so that the free end of the shaft extends perpendicularly from the angled surface. Linkow further shows a prosthetic tooth anchor threaded onto the free end of the shaft, to secure the collar in a fixed orientation. The Linkow apparatus and method, although directed to an alignment issue, is relatively complex and may have insufficient structural rigidity for some applications.

While the above-identified and other references describe apparati and methods for aligning prosthetic teeth and other dental appliances, there are various shortcomings. One is complexity of the apparatus. Another includes the difficulty of installation. Other shortcomings include screw access holes on the chewing surfaces of the prosthetic teeth, and limited serviceability of wear components.

SUMMARY OF THE INVENTION

An anchor apparatus according to the present invention comprises an implant anchor having a threaded post and an upper circular receptacle, and further comprises a support having a lower circular base having a first longitudinal axis and an upper female prosthesis eyelet, or receptacle, having a second longitudinal axis, the second longitudinal axis and the first longitudinal axis forming a mounting angle with respect to one another, wherein the circular base of the angled support is secured within the upper circular receptacle of the implant anchor.

A further aspect of an anchor apparatus according to the present invention comprises the circular base of the angled support being secured within the upper circular receptacle of the implant anchor by an interference fit and an adhesive.

Another aspect of an anchor apparatus of this invention is in accordance with any of the above-summarized aspects, further comprising a dental prosthesis having a male extension shaped for cooperative engagement with the upper female prosthesis receptacle of the implant anchor, wherein the dental prosthesis is secured to the implant anchor by such cooperative engagement.

The present invention provides a method for anchoring an appliance into an oral cavity having a step of threading an implant anchor having a threaded post into a bone, the implant anchor having an upper circular receptacle, applying an adhesive to an angled support, the angled support having a lower circular base and an upper female prosthesis receptacle, the circular base having a first longitudinal axis and the upper female prosthesis receptacle having a second longitudinal axis, the second longitudinal axis and the first longitudinal axis forming a mounting angle with respect to one another, inserting the circular base of the angles support into the circular receptacle, rotating the circular base about the first longitudinal axis within the circular receptacle until the second longitudinal axis points in a desired direction, and allowing the adhesive to set.

A further aspect of the method of this invention is in accordance with the previously summarized method, further comprising the additional step providing a dental prosthesis having a male extension shaped for cooperative engagement with the upper female prosthesis receptacle of the implant anchor, and attaching the dental prosthesis by such cooperative engagement.

A still further aspect of the method of this invention is in accordance with any of the previously summarized methods, and further comprising the steps of providing a plurality of the angled supports, each of the plurality having a respective mounting angle; providing an alignment apparatus; inserting the alignment apparatus into the female prosthesis receptacle to determine which of the plurality of angled supports achieves a desired position for a dental prosthesis, and using the determined angled support for the steps of applying an adhesive and inserting the circular base of the angles support into the female prosthesis receptacle.

In view of the above-identified and other shortcomings in the prior art, an object of the present invention is a dental appliance anchor having a simple but strong structure that is easy to install.

Another object is a dental appliance anchor that provides ready adjustability in orientation and position.

Another object is a dental appliance anchor in which wear components can be readily replaced without a complete removal of the anchor.

These and other objects, features and advantages of the present invention will become more apparent to, and better understood by, those skilled in the relevant art from the following more detailed description of the preferred embodiments of the invention taken with reference to the accompanying drawings, in which like features are identified by like reference numerals.

BRIEF DESCRIPTION OF THE DRAWINGS

FIG. 3 is a side projection view of an implant anchoring member of the FIG. 1 apparatus, prior to assembly, FIG. 4 is a cut-away enlargement view of the female circular receptacle and portion of the threaded shaft of the FIG. 3 implant anchoring member, seen from cut line "5-5";

DETAILED DESCRIPTION OF THE INVENTION

1. Overview

Figure 1:
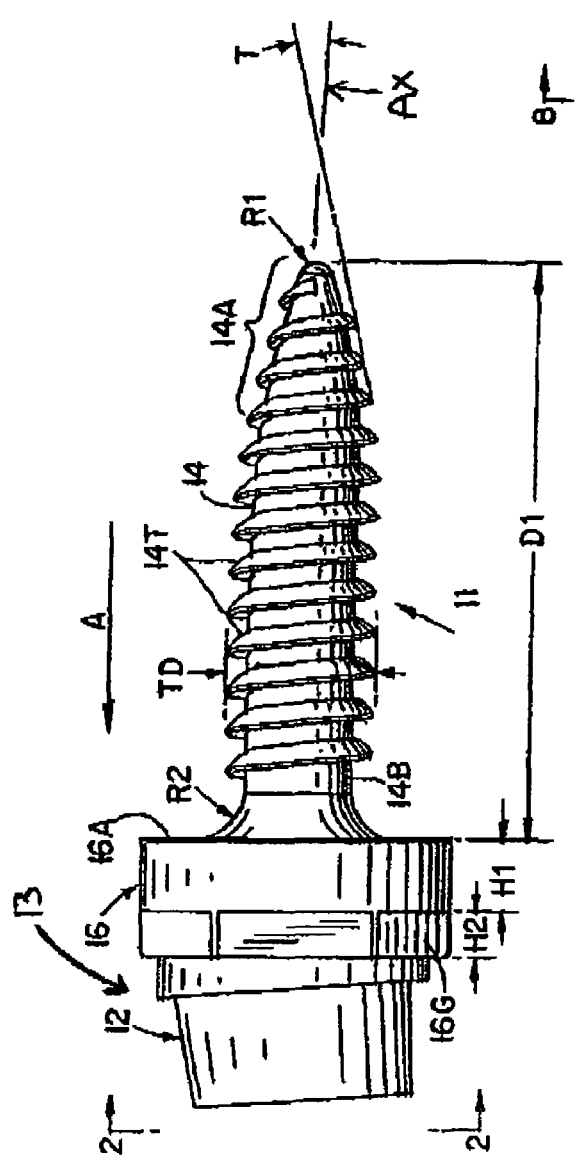
FIG. 1 is a side projection view of an assembled anchoring apparatus according to the present invention.

An example anchoring apparatus according to a first aspect of the present invention will be described in reference to FIGS. 1-7. FIG. 1 shows one variation of the example of FIG. 1-7 after assembly in an oral cavity as described herein. FIGS. 2-7 show examples of, and are used for description of, the two major components of the FIG. 1 assembly, which are the anchor implant member, labeled as item 11 in FIG. 1, and the upper removable support member, labeled as item 13 in FIG. 1. The relative position labels of "above" and below are in reference to the "A" direction line shown in FIG. 1, with an item "above" another item meaning the former to have a position further in the "A" direction. Example methods according to the present invention, by which an apparatus as shown in FIG. 1 is secured and assembled within an oral cavity, will be described.

Figure 9:
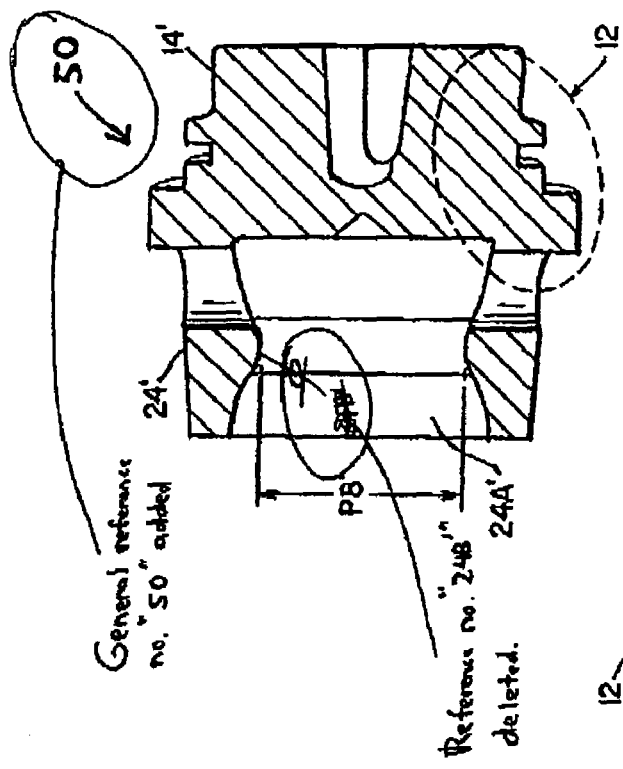
FIG. 9 is cut-away projection of an embodiment of this invention having a zero degree female eyelet integral with the threaded implant.

FIG. 9 depicts an example implant anchoring apparatus according to a second aspect of the present invention. The aspect that FIG. 9 examples includes in a single anchor member the functions of anchor implant member 11 and the upper removable support member 13 of the FIG. 1 assembly embodiment. As will be understood, the aspect of FIG. 9 is limited to, but exploits, installations where the optimal angle between the FIG. 1 anchor implant member and the FIG. 1 upper removable support member is zero degrees.

2. Detailed Description

Figure 2:
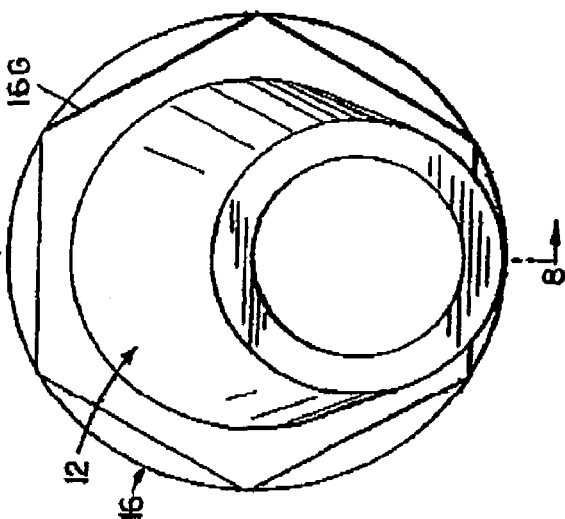
FIG. 2 is a top projection view of the assembled anchoring apparatus of FIG. 1, seen from view line "12-2"

FIG. 1 shows a side view of an example of an anchoring apparatus after installation and assembly according to the method of the present invention. FIG. 2 shows a perspective of the FIG. 1 example, seen from view line "2-2".

The FIG. 1 apparatus comprises an implant anchor member, labeled as item 11, and an upper angled support member, labeled as item 13. The implant anchor member 11 comprises a threaded shaft 14 and a receptacle base 16. An example is described in greater detail in reference to FIGS. 3-4. The FIG. 1 apparatus is assembled as it is installed in an oral cavity, as will be described. After installation, the implant anchor member 11 is substantially below the gum line (not shown), with the threaded portion 14 threaded into an underlying bone Referring to FIGS. 1 and 3, an example implant anchor member 11 is a unitary metal structure, preferably formed of a titanium-aluminum-vanadium alloy, having a threaded shaft 14 and an upper support 16. The threaded shaft has an outer thread diameter of TD, and preferably has a tapered end 14A, the tapered end having, for example, a taper angle of T degrees blending to a radius R1. Example values for these dimensions are TD=2.21 millimeters; R1=0.25 millimeters; and T=12 degrees. The taper T and radius R1 are for improved self-threading and implant into bone. The threaded shaft 14 extends a distance D1 from a lower surface 16A of the upper support 16. Preferably, for purposes of strength, a radius R2 merges the base 14B of the threaded shaft 14 to the surface 16A. Example values are D1=10, 13 or 15 millimeters, and R2=0.75 millimeters.

As shown in FIG. 1, the upper support portion 16 of the implant anchor 11 has a first height H1 in the "A" direction, and has a gripping surface 16G formed on an outside upper portion for a second height H2. Example values are H1=1.22 millimeters; and H2=0.77 millimeters. As will be described, the gripping surface 16G is for a wrench (not shown) to engage and apply rotation to the implant anchor member, for threading it into a bone.

FIG. 3 shows a side view of an example implant anchor 11 before insertion of the angled support 13. As seen in FIG. 1, the gripping portion 16G of the depicted example implant anchor 11 has a hexagonal shape. The hexagonal shape is for purposes of example only. Other shapes contemplated by the invention include, but are not limited to, square, two-sided, and pentagonal.

FIG. 4 shows a cut-away elevation view of the upper support 16 section of the implant anchor 11 of FIGS. 1 and 3 and a portion of the threaded shaft 14, seen from the cut-line "5-5". Formed within the upper support 16 is a female receptacle 18. The female receptacle 18 is preferably a circular receptacle having a major depth DP1 and a ridge 18R spaced by an under-cut 18U from the bottom surface 18L.

As will be understood from the description below, the undercut 18U functions as a reservoir for adhesive that is used during the assembly operation. As will also be understood, the function of the female receptacle 18 is to accommodate, and secure from axial movement during positioning, a base 20 of the upper angled support member 13, while allowing temporary rotation of the member about its axis AX. For these and other reasons, it will be understood that the specific form and dimension of the ridge 18R and undercut 18U is dictated, in part, by the form and dimension of the base 20.

Figure 7:
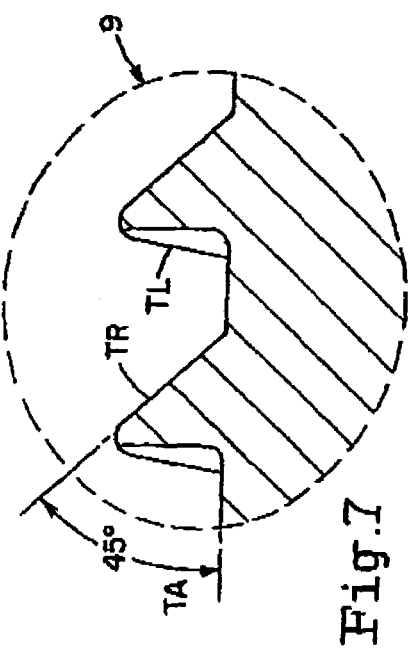
FIG. 7 is an enlargement of the view area in FIG. 4 labeled "9"
Figure 8:
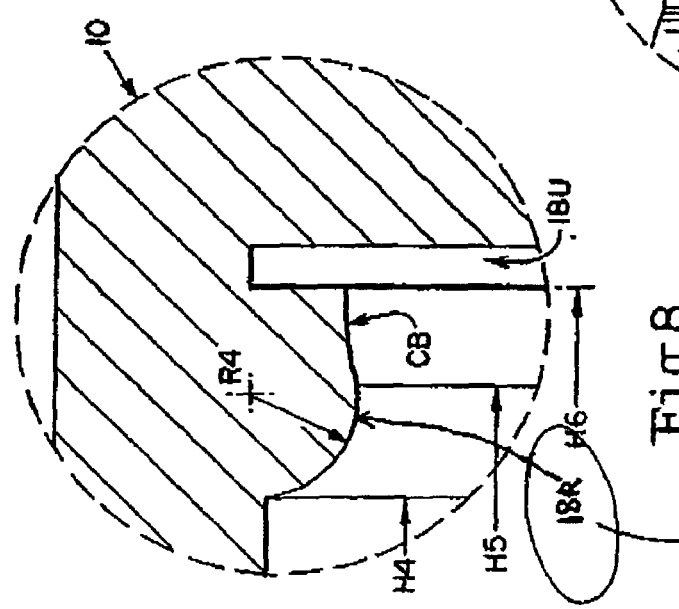
FIG. 8 is an enlargement of the view area in FIG. 4 labeled "10"

Referring to FIG. 4 and FIG. 8, where FIG. 8 shows a detailed view of the FIG. 4 labeled area 10, the depicted example female receptacle 18 has an undercut 18U extending from the lowermost surface of the receptacle 18, labeled 18L, to a point H3 below the upper surface 18H. The diameter of the undercut 18U is labeled DM1. The ridge 18R preferably has a radius R4 and a cut-back CB. As will be understood from FIGS. 6 and 7 described below, the cut-back CB permits the sections 20A through 20D to expand and, thus, lock into engagement with the receptacle 18.

The radius R4 of the depicted example begins at a height H4 below the upper surface 18H and ends at point H5, with the cut-back CB extending down to H6. The inner diameter DM2 formed by the ridge 18R is for an interference fit with the lower base 20 of the angled support member 13, as described in greater detail below. The interference fit is preferably firm, yet should permit rotation of the extension 13 about the axis AX prior to the adhesive setting, as described below. Therefore, the inner diameter DM2 is preferably held to a close tolerance, such as, for example, plus or minus 0.005 millimeters. Above the ridge 18R is a larger circular opening, having a diameter DM3, with a radius R5 at its opening to facilitate insertion of the base 20.

Example values for the above-identified dimensions are DP1=1.49 millimeters; DM1=3.56 millimeters, with an example tolerance of plus or minus 0.025 millimeters; DM2=2.97 millimeters, with an example tolerance of plus or minus 0.005 millimeters; R4=0.307 to 1.05 millimeters; F=0.25 millimeters; R5=0.15 millimeters; H3=0.77 millimeters, with an example tolerance of plus or minus 0.005 millimeters; H4=1.07 millimeters; H5=1.36 millimeters; and H6=1.48 millimeters.

FIG. 7 shows an enlargement of the threads 14T within the region of FIG. 7 labeled "9". As seen from FIG. 7, the threads 14T preferably have a substantially flat top land TL, with a lower land TR that is angled by TA degrees, with a typical TA value being 45 degrees.

It will be understood that the example receptacle 18 described above is for purposes of explaining the operation of, and providing general guidance in the practicing of this invention. Upon reading this disclosure, other structures for the receptacle 18 which provide for rotation of the angled support 12 prior to setting of its adhesive can be readily identified by persons skilled in the art.

Figure 6:
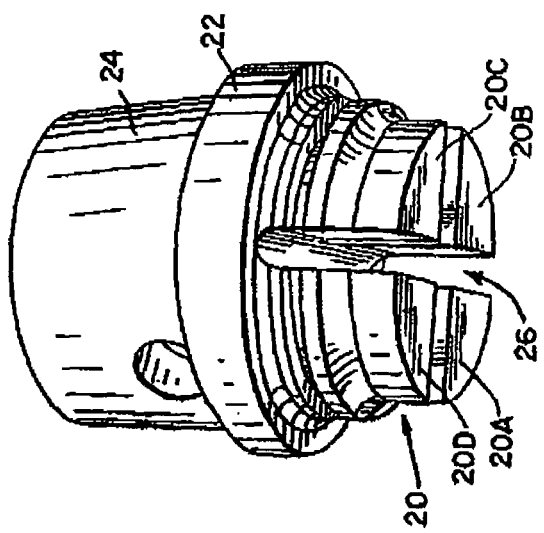
FIG. 6 shows a perspective view of the example upper female eyelet shown by FIG. 5 detailing its slotted lower base.
Figure 5:
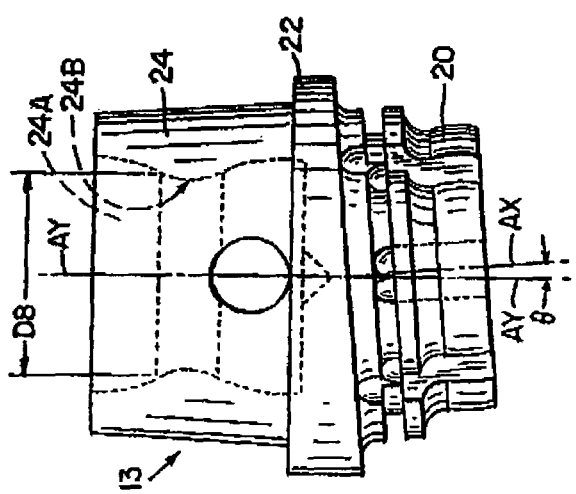
FIG. 5 is a side projection view of an example upper female eyelet of the FIG. 1 anchor apparatus.

FIGS. 5 and 6 show, in a side projection and perspective view, an example upper angled support 13. The example angled support 13 includes a slotted lower base 20, a wedge mid-base 22, and an upper angled female eyelet 24. Referring to FIG. 5, the upper angled female eyelet 24 includes a cavity 24A with a ridge 24B. The inner diameter at the ridge 24B is labeled D8. The cavity 24A and ridge 24B, in accordance with the diameter D8, securely hold a dental prosthesis such that depicted by U.S. Pat. No. 5,195,181, issued to Sulc, ("Sulc '181"), and U.S. Pat. No. 4,540,367, issued to Sulc ("Sulc '367"), both of which are hereby incorporated by reference, by engagement with its male extension installed in a recess at the bottom of the prosthesis.

The slotted lower base 20 of the angled support 13 preferably has multiple sections, which can resiliently move in the radial direction R when the base 20 is inserted into the circular receptacle 18 of the anchor implant 10, as is described below. The depicted example has four sections, labeled 20A, 20B, 20C and 20D, separated by slots 26.

The slotted lower base 20 and wedged mid-base 22 are substantially circular about an axis AX. The upper surface 22A of the wedged mid-base 22, as can be seen in FIG. 5, supports the female eyelet 24 at an angle THETA, which is measured between the axis AX and the axis AY of the female eyelet 24. As described below, a method according to this invention contemplates selection of the desired THETA angle at the time the described apparatus is installed into an oral cavity. The present inventor has identified example sets of THETA angles which keeps the inventory manageable yet accommodates a wide and acceptable range of requirements. A preferable set of THETA angles is 0, 5, 11 and 17 degrees. This set, however, is not a limitation, as others may be identified and used by persons skilled in the art.

A preferred material for the angled support member 13 is a titanium alloy.

Sulc '181 and Sulc '367 show a dental prosthesis having a male extension which is placed over and engaged into the female eyelet 13.

As described in Sulc '181 and Sulc '367, the male extension within the dental prosthesis is preferably formed of a plastic material having sufficient strength and durability to permit repeated connection and disconnection with the female eyelet 13. In addition, the material of the male extension should develop a retaining friction between it and the material of the female eyelet 13 to maintain attachment of the male extension and, accordingly, the attachment of the dental prosthesis. Further, the material of the extension 30 should permit removal and reinsertion of the male cap when desired. This is preferred because the male extension typically absorbs wear due to time and chewing forces and, as a result, should be periodically replaced. An example material for the male extension is strong nylon. An example replacement technique by which one male cap is removed and replaced by another is described the Sulc '367 patent.

An example method for installing an anchor, using the implant anchor 11 and angled upper support 13 of this invention, will be described.

First, the installation site is prepared using established methods within the dental and oral surgery arts. Next, the bone is pre-drilled, using a drill bit diameter and drilling depth selected by one skilled in the relevant arts. The tapered end 14A of the threaded shaft 14 of the implant anchor 11 is then placed into the drilled area and, using a wrench corresponding to the grip 16G, the implant anchor 11 is screwed into the bone until the surface 16A is at the desired height.

Next, using the alignment handle described as item 50 in the Sulc '181 patent, or by direct visual inspection, an appropriate THETA angle for the angled upper support 13 is chosen. As described above, typical THETA angles are 0, 5, 11, and 17 degrees. Therefore, in a typical method according to this invention, the dentist or oral surgeon would have an assortment of angled upper supports 13, having THETA angles such as the examples identified above.

A dental prosthesis such as that shown in Sulc '181 having a male extension is then placed over and engaged into the female eyelet 13 as described above.

As described in the Sulc '181 patent, a temporary cap, such as the item labeled as item "40" therein, may be installed into the female eyelet 24 until a prosthesis becomes available.

Figure 10:
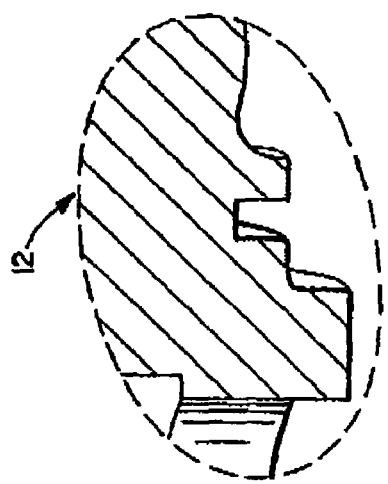
FIG. 10 is an enlargement of the view area in FIG. 9 labeled "12".

FIG. 9 shows a further aspect of this invention, which exploits the occasions when the optimal THETA angle is found to be zero degrees. In this situation there is no need to have separate members 11 and 13 and, accordingly, this aspect of the invention integrates the functions of those members, with respect to anchoring in bone and supporting a dental prosthesis, into a single member 50. FIG. 10 is a detailed view of the area in FIG. 9 labeled "12".

Referring to FIG. 9, an example of this aspect of the invention includes a single prosthesis support member 50 having a threaded structural portion 14' and an upper eyelet structural portion 24'. The portion 14' corresponds to, and may be identical to, the threaded shaft 14 of FIG. 4, and the portion 24' corresponds to the structure labeled as 24 in FIG. 5.

While the present invention has been disclosed with reference to certain preferred embodiments, these should not be considered to limit the present invention. One skilled in the art will readily recognize that variations of these embodiments are possible, each falling within the scope of the invention, as set forth in the claims below.

The invention claimed is:

1. A dental appliance anchor apparatus, comprising:
   an implant anchor having a tapered threaded post for engagement with a bone and an upper circular receptacle, the outside area of the upper circular receptacle having gripping portions for engaging with a tightening device, the upper receptacle having a lateral undercut reservoir for accepting an adhesive, wherein the threaded post includes threads that have a substantially flat top land; and
   an angled support having a slotted lower circular base and an upper female prosthesis receptacle for engaging a dental prosthesis, the slotted lower circular base having a first longitudinal axis and the upper female prosthesis receptacle having a second longitudinal axis, the second longitudinal axis and the first longitudinal axis forming a mounting angle with respect to one another, wherein the slotted lower circular base of the angled support is secured within the upper circular receptacle of the implant anchor wherein the angled support is rotatable within the upper circular receptacle for optimizing its position prior to being secured with the adhesive.

2. A dental appliance anchor apparatus according to claim 1, wherein the slotted lower circular base of the angled support is secured within the upper circular receptacle of the implant anchor by a combination of an interference fit in resilient engagement with the slotted lower circular base and the adhesive.

3. A dental appliance anchor apparatus according to claim 1, further comprising a dental prosthesis having a male extension shaped for cooperative engagement with the upper female prosthesis receptacle of the implant anchor, wherein the dental prosthesis is secured to the implant anchor by such cooperative engagement.

4. A dental appliance anchor apparatus according to claim 1 wherein said implant anchor is a unitary metal structure.

5. A dental appliance anchor apparatus, comprising:
   an implant anchor having a tapered threaded post for engagement with a bone and an upper receptacle, the outside area of the upper receptacle having gripping portions for engaging with a tightening device, the upper receptacle having a lateral undercut reservoir for accepting an adhesive, wherein the tapered threaded post includes threads that have a substantially flat top land; and
   an angled support having a slotted lower base and an upper support for engaging a dental prosthesis, the slotted lower base having a first longitudinal axis and the upper support having a second longitudinal axis, the second longitudinal axis and the first longitudinal axis forming a mounting angle with respect to one another, wherein the slotted lower base of the angled support is secured within the upper receptacle of the implant anchor by an adhesive, and wherein the slotted lower base of the angled support and the upper receptacle are constructed and arranged such that the lower base of the angled support rotates within said upper receptacle, about said first longitudinal axis, prior to being secured by said adhesive.

* * * * *